US012161448B2

(12) United States Patent
Iegaki et al.

(10) Patent No.: US 12,161,448 B2
(45) Date of Patent: Dec. 10, 2024

(54) BIOLOGICAL INFORMATION DETECTION DEVICE WITH SENSOR AND CONTACT PORTIONS TO BRING SENSOR INTO CONTACT WITH PORTION OF EAR

(71) Applicant: CASIO COMPUTER CO., LTD., Tokyo (JP)

(72) Inventors: Yuichiro Iegaki, Kodaira (JP); Masahiro Maeda, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 448 days.

(21) Appl. No.: 17/022,265

(22) Filed: Sep. 16, 2020

(65) Prior Publication Data

US 2021/0085193 A1    Mar. 25, 2021

(30) Foreign Application Priority Data

Sep. 24, 2019    (JP) ................................. 2019-172673
Jun. 8, 2020      (JP) ................................. 2020-099486

(51) Int. Cl.
*A61B 5/026*       (2006.01)
*A61B 5/00*        (2006.01)

(52) U.S. Cl.
CPC ............ *A61B 5/026* (2013.01); *A61B 5/6817* (2013.01); *A61B 2560/04* (2013.01)

(58) Field of Classification Search
CPC .............................. A61B 5/6817; A61B 5/026
See application file for complete search history.

(56) References Cited

U.S. PATENT DOCUMENTS

2007/0135717 A1*  6/2007  Uenishi ................ A61B 5/6815
                                                600/509
2016/0023047 A1*  1/2016  Wisbey .............. A61B 5/02427
                                                434/247

(Continued)

FOREIGN PATENT DOCUMENTS

CN      101601583 A     12/2009
CN      109068994 A     12/2018
(Continued)

OTHER PUBLICATIONS

Notice of Reasons for Refusal dated Aug. 24, 2021 received in Japanese Patent Application No. JP 2020-099486 together with an English language translation.

(Continued)

*Primary Examiner* — Devin B Henson
*Assistant Examiner* — Evelyn Grace Park
(74) *Attorney, Agent, or Firm* — Scully, Scott, Murphy & Presser, P.C.

(57) ABSTRACT

A biological information detection device having a sensor, arranged in a main body, to detect biological information from a portion of a tragus facing an ear canal and a first contact portion and a second contact portion configured to bring the sensor into contact with the portion of the tragus, wherein the second contact portion includes a first end connected to the main body, a second end connected to the main body and an anthelix-side contact portion, disposed away from the main body and continuous with the first end and the second end, configured to contact an anthelix and/or a cymba canchae, wherein, in a state where the first contact portion contacts the cavum conchae, one of the first end and the second end that is closer to the ear canal is disposed closer to the first contact portion than the other of the first end and the second end.

6 Claims, 11 Drawing Sheets

(56) References Cited

U.S. PATENT DOCUMENTS

| | | | |
|---|---|---|---|
| 2017/0034615 A1* | 2/2017 | Mankodi | A61B 5/6843 |
| 2019/0029593 A1* | 1/2019 | Orron | H04R 1/105 |

FOREIGN PATENT DOCUMENTS

| | | | |
|---|---|---|---|
| JP | 2006-203420 A | 8/2006 |
| JP | 2009-290667 A | 12/2009 |
| JP | 2013-146371 A | 8/2013 |
| JP | 2017-225074 A | 12/2017 |
| JP | 2018-522497 A | 8/2018 |

OTHER PUBLICATIONS

First Office Action dated Apr. 28, 2023 received in Chinese Patent Application No. CN 202010944067.6.

* cited by examiner

BIOLOGICAL INFORMATION DETECTION DEVICE WITH SENSOR AND CONTACT PORTIONS TO BRING SENSOR INTO CONTACT WITH PORTION OF EAR

CROSS-REFERENCE TO RELATED APPLICATIONS

This application is based upon and claims the benefit of priority from prior Japanese Patent Application No. 2019-172673, filed Sep. 24, 2019, and Japanese Patent Application No. 2020-099486, filed Jun. 8, 2020, the entire contents of which are incorporated herein by reference.

FIELD

The present invention relates, for example, a biological information detection device configured to detect a blood flow by being worn on an ear.

BACKGROUND

For example, the blood flow sensor disclosed in Jpn. Pat. Appln. KOKAI Publication No. 2013-146371 is applied to an in-ear headphone, and includes a housing and an ear piece and sensor element provided in the housing. When the ear piece is inserted into an ear canal, the sensor element is in contact with the tragus, and detects a blood flow. The sensor element is supported by an elastic body provided in the housing. The elastic body is stretchable in a direction intersecting to the insertion direction of the ear piece into the ear canal, and presses the sensor element toward the tragus.

SUMMARY

As one aspect of the present invention, a biological information detection device includes a main body; a sensor fixed in the main body, brought into contact with the portion for detection, a tragus of a wearer on an ear canal side, and configured to detect biological information on a blood flow of the wearer; and at least one contact portion provided in the main body and configured to press the sensor against the portion for detection by exerting, on the main body, a reaction force on at least one of an anthelix and a cavum conchae of an ear of the wearer generated by contact with at least one of the anthelix and the cavum conchae.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Embodiments of the present invention will be described with reference to the accompanying drawings.

Figure 1:
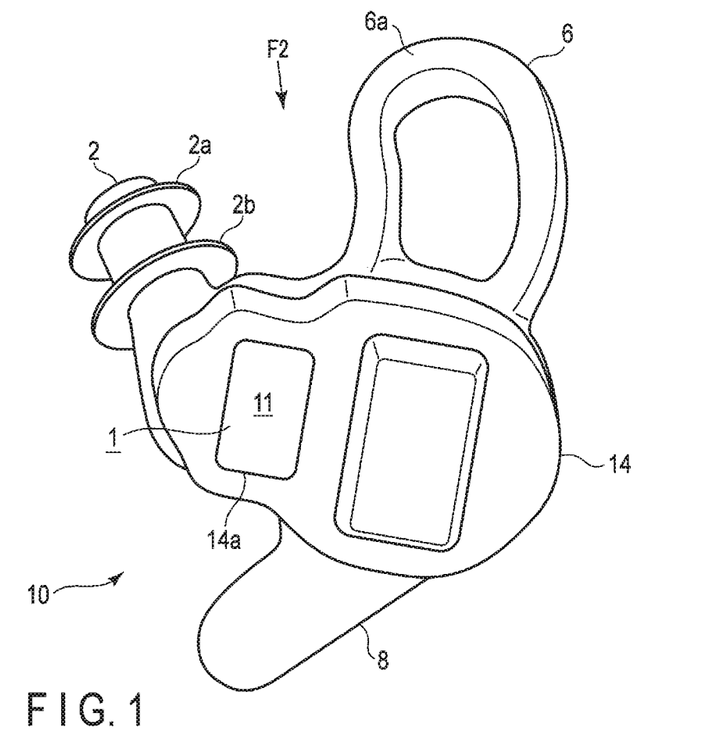
FIG. 1 is a perspective view showing a biological information detection device according to a first embodiment of the present invention.
Figure 2:
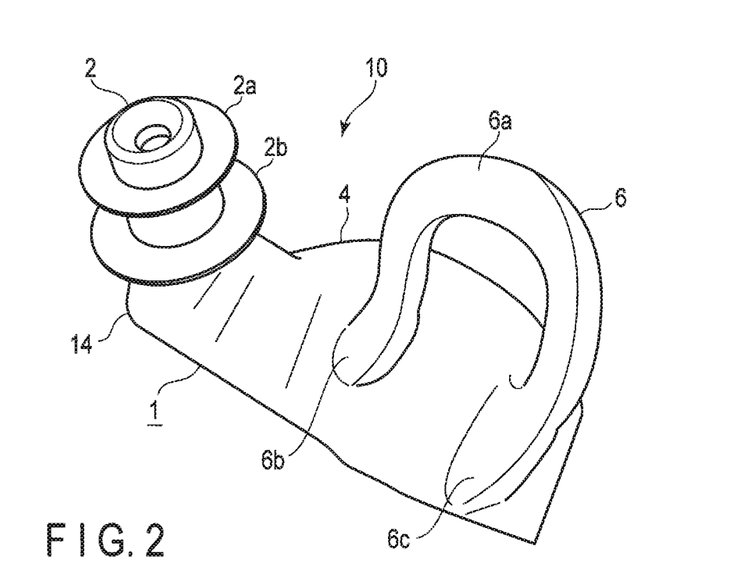
FIG. 2 is a perspective view of the biological information detection device in FIG. 1, viewed in the direction indicated by arrow F2.

As shown in FIGS. 1 and 2, a biological information detection device 10 (hereinafter also simply referred to as a "device 10") includes an insertion portion 2, a pressing portion 4 (contact portion, first contact portion), an engagement portion 6 (contact portion, second contact portion), a positioning portion 8, and a sensor 1.

Figure 3:
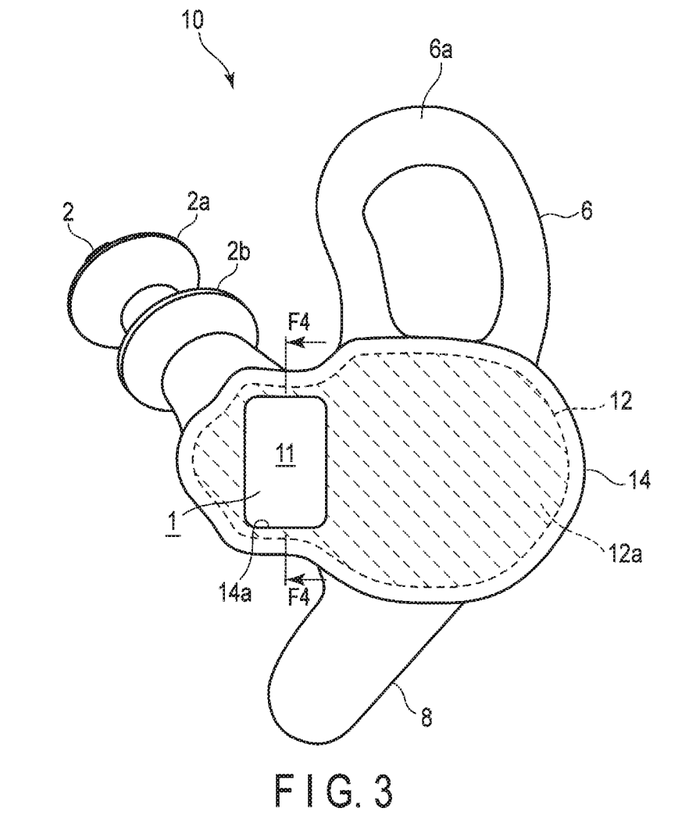
FIG. 3 is a view showing a main body of the biological information detection device in FIG. 1.

As shown in FIG. 3, the device 10 includes a main body 12 in which the sensor 1 is fixed, and a cover 14 which covers the exterior of the main body 12. The cover 14 is formed of an elastic member, such as an elastomer, and includes the above-described insertion portion 2, pressing portion 4, engagement portion 6, and positioning portion 8. Namely, the insertion portion 2, pressing portion 4, engagement portion 6, and positioning portion 8 are formed of an elastic member integrally with the cover 14. The main body 12 can be formed of a resin or a metal.

The cover 14 is detachably attached to the main body 12, and can be replaced with another cover 14 having a different size and shape. In other words, the shapes and sizes of the insertion portion 2, pressing portion 4, engagement portion 6, and positioning portion 8 can be changed by replacement of the cover 14, and commonality of the main body 12 is enabled.

Figure 4:
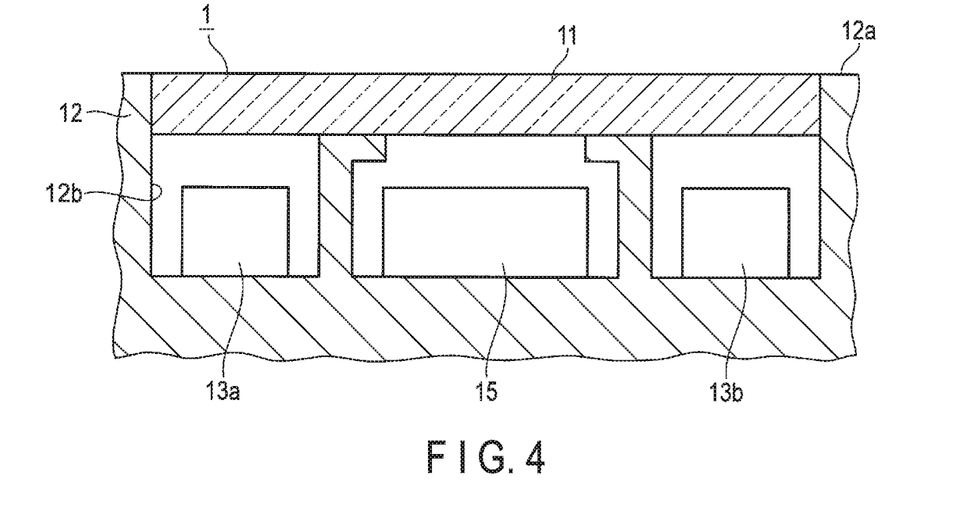
FIG. 4 is an enlarged cross-sectional view of the biological information detection device in FIG. 3, taken along line F4-F4.

As shown in FIGS. 3 and 4, the sensor 1 is buried in the main body 12. The sensor 1 is contained in a recess 12b on a surface 12a of the main body 12. The opening of the recess 12b on the surface 12a side of the main body 12 is closed by a transparent plate member 11. The plate member 11 herein is, for example, a transparent glass plate or acrylic plate. The plate member 11 is not limited to the above, and may be formed of a material that is a good transmitter of, for example, green light, red light, and infrared light. In FIG. 4, the cover 14 is omitted.

The sensor 1 includes two light emitting elements 13a and 13b, and one light receiving element 15. The light emitting elements 13a and 13b are, for example, LED elements, and are disposed on the bottom of the recess 12b with the light receiving element 15 interposed therebetween. Light emitted from the light emitting elements 13a and 13b is diffused in an ear, and the return light is received by the light receiving element 15. The sensor 1 is, for example, a reflective photoplethysmography (PPG) sensor configured to detect biological information on a blood flow, and detects a heart rate per unit time, or the like. As shown in FIGS. 1 and 3, the cover 14 includes an opening 14a to have the plate member 11 of the sensor 1 exposed to the outside.

Figure 5:
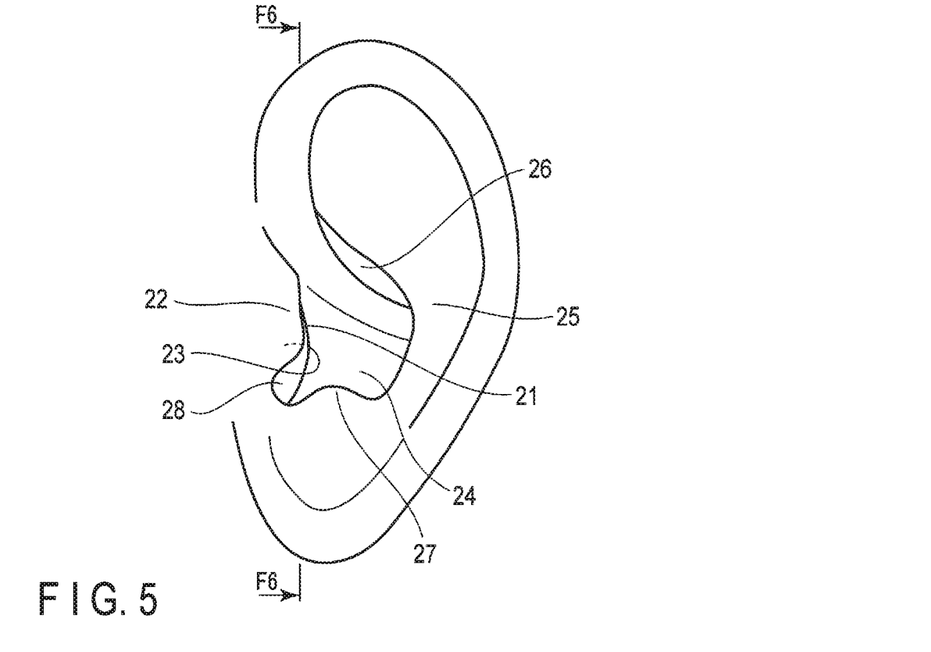
FIG. 5 is an external view of an exemplary left ear, showing the left side of the ear.
Figure 6:
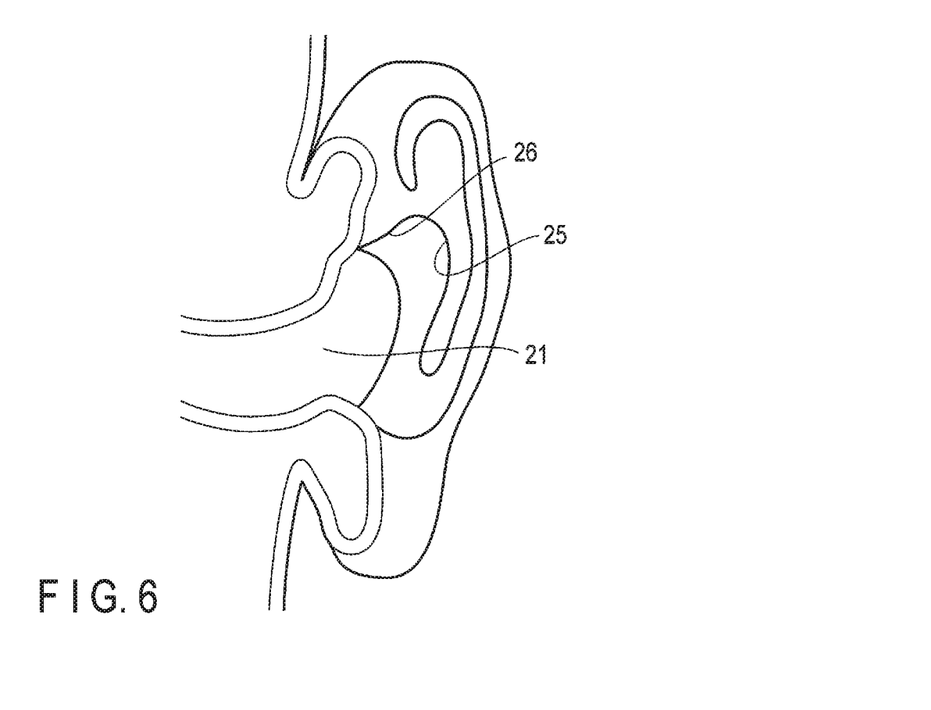
FIG. 6 is a cross-sectional view of the left ear in FIG. 5, taken along line F6-F6.

Hereinafter, the external form of the device 10 and a detailed structure of each component will be described with reference to FIGS. 5 to 8. The device 10 can be worn on an ear of a human being or anthropoid ape, such as a monkey or a chimpanzee. In the following description, the directions "up", "down", "right", "left", "front", "back", "inside", "outside", etc., are defined from the viewpoint of the wearer of the device 10. FIGS. 5 and 6 show an example of an average-size ear on which the device 10 is worn. In FIG. 6, hatching indicating a cross section of the ear is omitted for improved clarity.

The insertion portion 2 is inserted in the ear canal 21 of the ear. The insertion portion 2 is formed by a probe (not shown) formed integrally with the main body 12 to project therefrom in a given direction and part of the cover 14 which covers the exterior of the probe. The probe may be provided with a temperature sensor (not shown) at its tip, for example. The temperature sensor is, for example, a thermopile or a bolometer, and detects infrared light emitted from a detection object (such as an eardrum or skin therearound) in a noncontact manner, and converts it into a voltage. The device 10 measures a temperature of the detection object based on the intensity of the infrared light detected through the temperature sensor.

The angle of the probe, i.e., the insertion portion 2, with respect to the main body 12 is desirably set at an angle that brings the surface of the plate member 11 of the sensor 1 fixed in the main body 12 into surface contact with a portion 23 of a tragus 22 on the ear canal 21 side (hereinafter referred to as a "portion for detection 23") in a state where the insertion portion 2 is inserted in the ear canal 21 to a certain depth (state shown in FIG. 7). The shape of an ear varies between individuals; therefore, descriptions are provided herein with reference to an average ear shape shown in FIGS. 5 and 6 as an example. However, the probe may have, for example, a structure flexibly-bendable with respect to the main body 12 in accordance with the shape of the ear.

In general, the ear canal 21 extends obliquely upward from the outside to the inside of the ear. In contrast, assuming that the surface of the portion for detection 23 on the back of the tragus is flat, the line orthogonal to the surface is inclined to extend obliquely forward to the outside. Namely, the insertion direction of the insertion portion 2 into the ear canal 21 is different from the pressing direction of the sensor 1 to the portion for detection 23. In other words, the portion for detection 23 is angled with respect to the ear canal 21. Just as the shape of an ear varies between individuals, so does the angle of the portion for detection 23 with respect to the ear canal 21.

Since the eardrum (not shown) is not visible when the ear canal 21 is viewed from outside, it can be understood that the entrance of the ear canal 21 is partly covered by the tragus 22. Accordingly, the surface of the plate member 11 of the sensor 1 is pressed against the portion for detection 23 on the back of the tragus only by the insertion portion 2 being inserted and disposed in the ear canal 21.

The insertion portion 2 approximately coaxially includes two approximately-annular holding pieces 2a and 2b formed integrally with the cover 14. The two holding pieces 2a and 2b are apart from each other in the longitudinal direction of the insertion portion 2. When the insertion portion 2 is inserted into the ear canal 21, the two holding pieces 2a and 2b are brought into contact with the inner surface of the ear canal 21 with elastic deformation, and achieve a stable wear state of the insertion portion 2 with respect to the ear canal 21. Namely, the two holding pieces 2a and 2b enable the insertion portion 2 to be tightly held with respect to the ear canal 21, thus inhibiting the insertion portion 2 from being dislodged from the ear canal 21.

Figure 7:
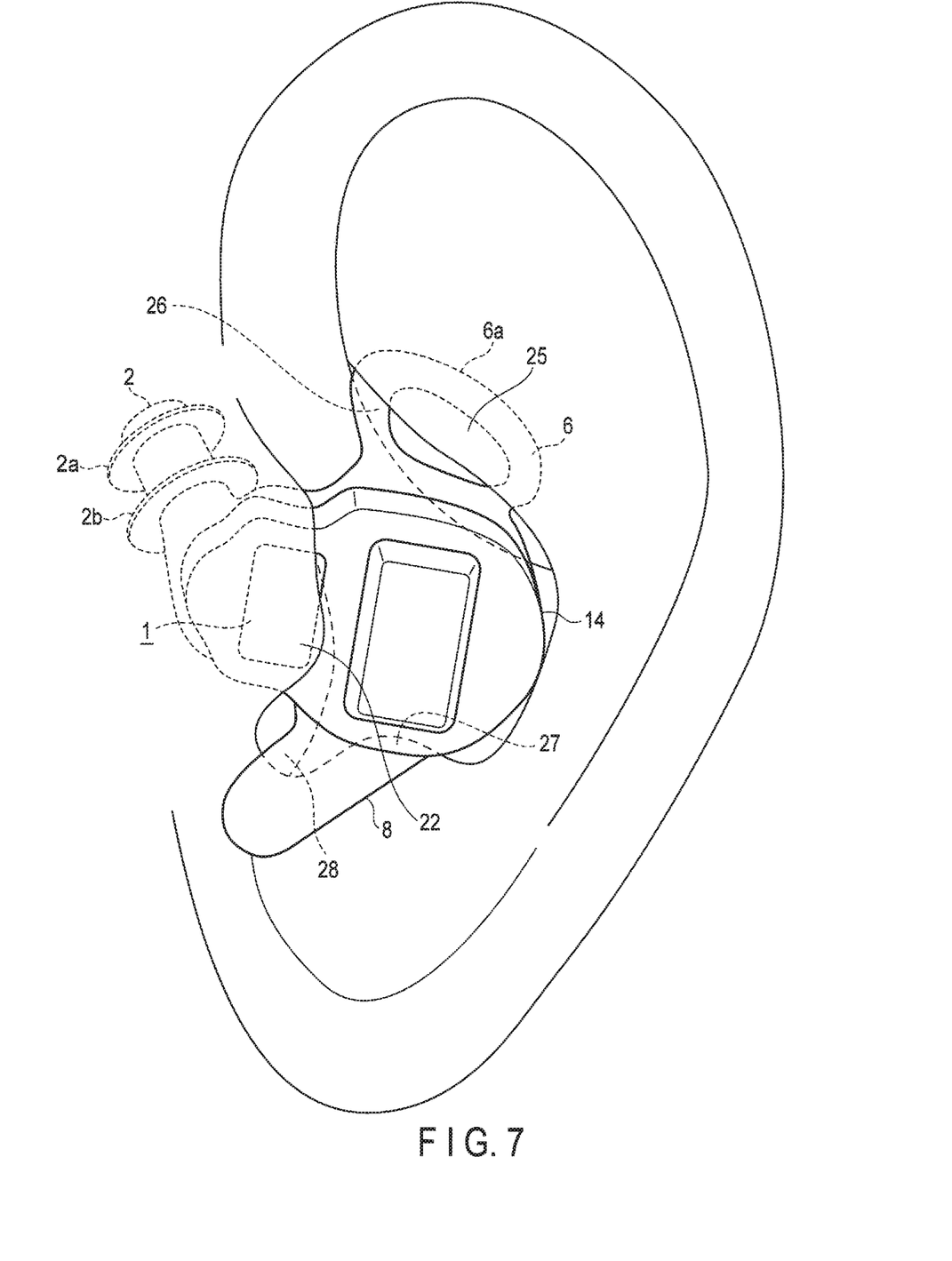
FIG. 7 is an external view showing a state where the biological information detection device in FIG. 1 is worn on the ear in FIG. 5.

The pressing portion 4 is provided at a position that makes the pressing portion 4 come into contact with a cavum conchae 24 in the state where the insertion portion 2 is inserted into the ear canal 21 (FIG. 7). The pressing portion 4 has a shape such that the cover 14 bulges out like a dome toward the cavum conchae 24. The pressing portion 4 is of a size such that the pressing portion 4 is brought into approximately the entire surface of the cavum conchae 24. The pressing portion 4 is a solid or hollowed-out elastic member.

Figure 8:
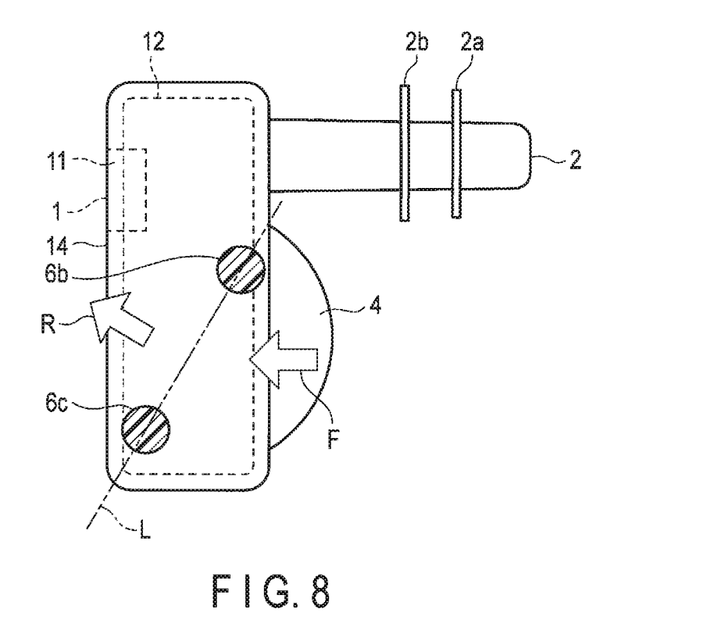
FIG. 8 is a diagram for explaining a function of a pressing portion of the biological information detection device in FIG. 1.

The pressing portion 4 is pressed against the cavum conchae 24 by the insertion portion 2 being inserted into the ear canal 21, and is elastically deformed upon contact. The reaction force of the cavum conchae 24 generated by the contact of the pressing portion 4 with the cavum conchae 24 acts to press the sensor 1 against the portion for detection 23 on the back of the tragus. Specifically, as shown in FIG. 8, the reaction force F of the cavum conchae 24 received by the pressing portion 4 acts to rotate the main body 12 to the tragus 22 side (indicated by arrow R in the figure) about a point around the base of the insertion portion 2 on the main body 12 side, thereby pressing the sensor 1 against the portion for detection 23. At this time, since the insertion portion 2 is inserted into the ear canal 21, the rotation is performed about a point around the base of the insertion portion 2.

The engagement portion 6 is, for example, a rod-like elastic member bent in a U-shape. The engagement portion 6 is formed integrally with the cover 14 in such a manner that a curved portion 6a (antihelix-side contact portion) of the U-shape is disposed away from the main body 12. Namely, the engagement portion 6 has one end 6b and the other end 6c (FIG. 8) provided on the main body 12 side, and includes a curved portion 6a (contact portion) continuous with those two ends 6b and 6c and in contact with an antihelix 25.

In the state where the insertion portion 2 is inserted into the ear canal 21 (state shown in FIG. 7), the curved portion 6a at the tip of the engagement portion 6 with respect to the projecting direction is made to fit between the antihelix 25 and a cymba conchae 26 with elastic deformation, and thus is brought into contact with both 25 and 26. In this state, the curved portion 6a of the engagement portion 6 is disposed inside the antihelix 25, and is at least partly covered with the antihelix 25.

In the state shown in FIG. 7, the engagement portion 6 is elastically deformed by the curved portion 6a fitting between the antihelix 25 and the cymba conchae 26 and brought into contact with them both. The reaction forces of the antihelix 25 and cymba conchae 26 generated by the contact of the engagement portion 6 with the antihelix 25 and cymba conchae 26 act to press the sensor 1 against the portion for detection 23 on the back of the tragus. Like the above-described reaction force F of the cavum conchae 24, the reaction forces of the antihelix 25 and cymba conchae 26 received by the engagement portion 6 at this time act to rotate the main body 12 about a point around the base of the insertion portion 2.

By forming the engagement portion 6 of an elastically deformable material, the reaction force of the antihelix 25 (and the cymba conchae 26) can be exerted on the main body 12 without causing the engagement portion 6 to be dislodged from the antihelix 25, and the sensor 1 can be pressed against the portion for detection 23.

Since ear shapes vary between individuals, the curved portion 6a of the engagement portion 6 may not fit deeply into the cymba conchae 26. For example, when the device 10 is worn on a relatively large ear and the insertion portion 2 is inserted into the ear canal 21, the curved portion 6a may be only slightly caught by the antihelix 25 and may not reach the cymba conchae 26. In such a case, the engagement portion 6 is elastically deformed by being brought into contact with the antihelix 25. As in the above-described case, the reaction force of the antihelix 25 generated by the contact of the engagement portion 6 with the antihelix 25 acts to rotate the main body 12 about a point around the base of the insertion portion 2, thereby pressing the sensor 1 against the portion for detection 23.

In any case, according to the present embodiment, the engagement portion 6 is brought into contact with the antihelix 25 and cymba conchae 26 or with the antihelix 25 only, and the reaction forces of the antihelix 25 and cymba conchae 26 thereby generated act to press the sensor 1 against the portion for detection 23 via the main body 12.

To press the sensor 1 against the portion for detection 23 well, the ends 6b and 6c of the engagement portion 6 are disposed so that the end 6b closer to the insertion portion 2 (on the wearer's ear canal side) is disposed closer to the cavum conchae 24 (closer to the pressing portion 4) than the other end 6c, as shown in FIGS. 2 and 8. In other words, the engagement portion 6 is provided so that an imaginary line L (FIG. 8) connecting the ends 6b and 6c of the engagement portion 6 is inclined with respect to the surface of the plate member 11 of the sensor 1. Accordingly, the reaction forces of the antihelix 25 and cymba conchae 26 can be sufficiently exerted onto the portion for detection 23 via the engagement portion 6 and the main body 12, and the sensor 1 can be reliably pressed against the portion for detection 23.

The engagement portion 6 is not limited to a rod-like elastic member bent in a U-shape, and may be a rod-like elastic member bent in an L-shape or any other shape that can generate a force in a direction that presses the sensor 1 against the portion for detection 23 using the reaction force generated upon elastic deformation. In any case, it is desirable that the engagement portion 6 has a projection length longer than the projection length of the insertion portion 2 from the main body 12 in order that the sensor 1 is sufficiently pressed against the portion for detection 23.

As described above, the pressing portion 4 and the engagement portion 6 function as contact portions for pressing the sensor 1 against the portion for detection 23. Therefore, although only one of the pressing portion 4 and the engagement portion 6 is provided, the sensor 1 can be sufficiently pressed against the portion for detection 23; however, when both of the pressing portion 4 and the engagement portion 6 are provided, the sensor 1 can be more reliably pressed against the portion for detection 23 than in the case where only one of the pressing portion 4 and the engagement portion 6 is provided.

The positioning portion 8 is provided at a position that makes the positioning portion 8 come into contact with an incisura intertragica 28 between the tragus 22 and an antitragus 27 in the state where the insertion portion 2 is inserted into the ear canal 21. In other words, the positioning portion 8 is provided at a position and angle with respect to the main body 12 which make the positioning portion 8 fit into the incisura intertragica 28 in the state where the insertion portion 2 is inserted into the ear canal 21. The positioning portion 8 is a projection integral with the cover 14, which extends straight forwards in a given direction from the main body 12.

The positioning portion 8 is fitted into the incisura intertragica 28 by the insertion portion 2 being inserted into the ear canal 21, and is elastically deformed upon contact. The reaction force of the incisura intertragica 28 generated by the contact of the positioning portion 8 with the incisura intertragica 28 acts to press the sensor 1 against the portion for detection 23 on the back of the tragus. Specifically, when the device 10 is worn on a left ear, the reaction of the incisura intertragica 28 acts in a direction that moves the device 10 leftward away from the head of the wearer. In other words, like the above-described reaction force F of the cavum conchae 24, the reaction force of the incisura intertragica 28 acts to rotate the main body 12 about a point around the base of the insertion portion 2. Accordingly, the sensor 1 is pressed against the portion for detection 23. The positioning portion 8 also has a function of positioning the device 10 with respect to the ear by fitting into the incisura intertragica 28.

Figure 9:
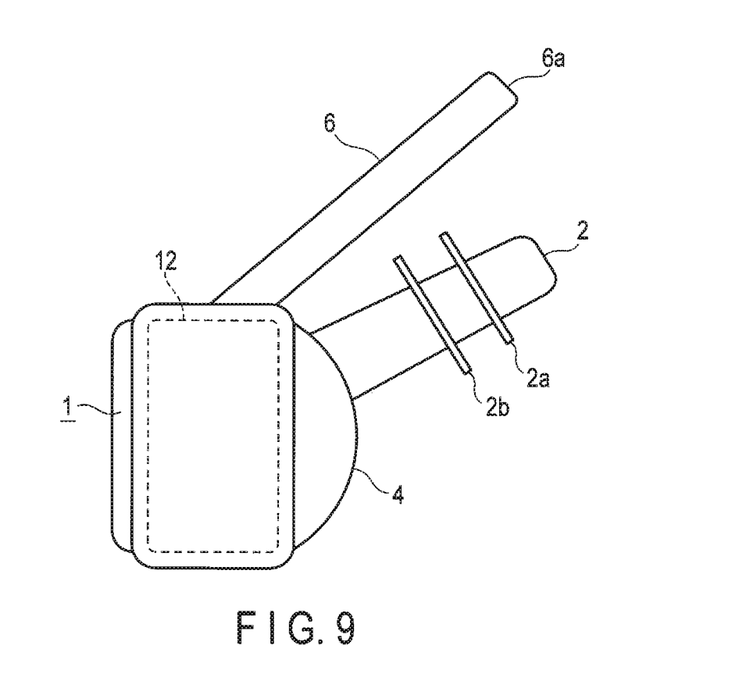
FIG. 9 is a schematic view showing a modification of the biological information detection device in FIG. 1.

By providing the device 10 with the positioning portion 8 in addition to the pressing portion 4 and engagement portion 6, the device 10 can be worn in such a manner as to better fit the ear, and the sensor 1 can be more reliably pressed against the portion for detection 23 on the back of the tragus. However, the positioning portion 8 is not an essential structure for the present invention, and may be omitted as in the modification shown in FIG. 9. As described above, the device 10 may be provided with at least one of the pressing portion 4 and the engagement portion 6 and need not necessarily be provided with both of them.

As described above, the device 10 according to the present embodiment includes the pressing portion 4 and the engagement portion 6 as contact portions for pressing the sensor 1 against the portion for detection 23 on the back of the tragus, and thus can more reliably press the sensor 1 against the portion for detection 23 and can improve the blood flow detection accuracy. Consequently, according to the present embodiment, reliability in blood flow detection can be improved. Namely, the device 10 of the present embodiment has a structure in which the sensor 1 is fixed in the main body 12, and does not have a mechanism for moving the sensor 1 with respect to the main body 12; therefore, there is no undesirable gap between the sensor 1 and the main body 12, and a malfunction is not caused by entry of a foreign body, such as dust, into the gap.

The above-described advantage of the present embodiment is enhanced by providing the device 10 with both of the pressing portion 4 and the engagement portion 6, but can also be produced by providing the device 10 with only one of the pressing portion 4 and the engagement portion 6. The presence of the positioning portion 8 can provide not only the function of positioning the device 10 with respect to the ear, but also the function of pressing the sensor 1 against the portion for detection 23, and can further improve the detection accuracy.

The device 10 including both of the pressing portion 4 and the engagement portion 6 as in the present embodiment can generate a force to press the sensor 1 against the portion for detection 23 due to the resultant force of a reaction force that the pressing portion 4 receives from the cavum conchae 24 and reaction forces that the engagement portion 6 receives from the antihelix 25 and the cymba conchae 26. Looked at from another perspective, the pressing force (reaction force) to press the sensor 1 against the portion for detection 23 is distributed among the cavum conchae 24, antihelix 25, and cymba conchae 26, and the pressing force applied to each of the cavum conchae 24, antihelix 25, and cymba conchae 26 by the device 10 can be reduced; accordingly, the wearer is less likely to feel pain even when the device 10 is worn on the ear for a long time.

In addition, providing the device 10 with the pressing portion 4 and the engagement portion 6 as contact portions for pressing the sensor 1 against the portion for detection 23 as in the present embodiment can make it easier for the device 10 to be worn tightly on the ear regardless of the size of the ear, which varies between individuals. Namely, even if one of the pressing portion 4 and the engagement portion 6 is not in close contact with the ear, the device 10 can be worn on the ear as long as the other is in close contact with the ear, thus allowing for variations in the shape and size of the ear.

For example, variations in ear shape and size can be factored in by designing one of the pressing portion 4 and the engagement portion 6 for a wearer with a relatively large ear, and designing the other for a wearer with a relatively small ear; as a result, multiple types of covers 14 need not be prepared for respective ear sizes.

In other words, even if the device 10 includes one of the pressing portion 4 and the engagement portion 6, the device 10 can be worn on any ear only by preparing multiple types of covers 14 for various shapes and sizes of ears, in which case a cover 14 suitable for the wearer can be selected and put on the main body 12.

The present invention has been described based on an embodiment; however, the present invention is not limited to the embodiment described above. Needless to say, various modifications or applications can be made without departing from the spirit of the present invention.

For example, described in the above embodiment is the case where the pressing portion 4, the engagement portion 6, and the positioning portion 8 are provided in the cover 14 that is placed on the main body 12 of the device 10; however, the present invention is not limited to this, and the cover 14 may be omitted, and the pressing portion 4, the engagement portion 6, and the positioning portion 8 may be provided integrally with the main body 12. In this case, the main body 12 itself may be formed by an elastically-deformable member, or the pressing portion 4, the engagement portion 6, and the positioning portion 8 may be formed by a member that is more resistant to elastic deformation, such as a rigid body. In the latter case, the device 10 can be worn on an ear by the ear being deformed in accordance with the shapes of the pressing portion 4, the engagement portion 6, and the positioning portion 8.

Described in the above embodiment is the case where the entire pressing portion 4, engagement portion 6, and positioning portion 8 are formed by an elastic member; however, the present invention is not limited to this case, and only the portions of the pressing portion 4, engagement portion 6, and positioning portion 8 that come into contact with the ear or the root portion between the main body 12 and each of the pressing portion 4, engagement portion 6, and positioning portion 8 may be elastic.

Described in the above embodiment is the device 10 including the sensor 1 for detecting biological information on a blood flow or a temperature sensor; however, the present invention is not limited to this, and may be applicable to a hearable device, such as an ear phone, not provided with such detection means. The present invention can also be applied to a hearable device, such as an ear phone, provided with such detection means.

Hereinafter, a biological information detection device 30 according to a second embodiment will be described with reference to FIGS. 10 to 12. Herein, the components having the same functions as those in the first embodiment will be assigned with the same reference numerals, and detailed descriptions thereof will be omitted.

Figure 10:
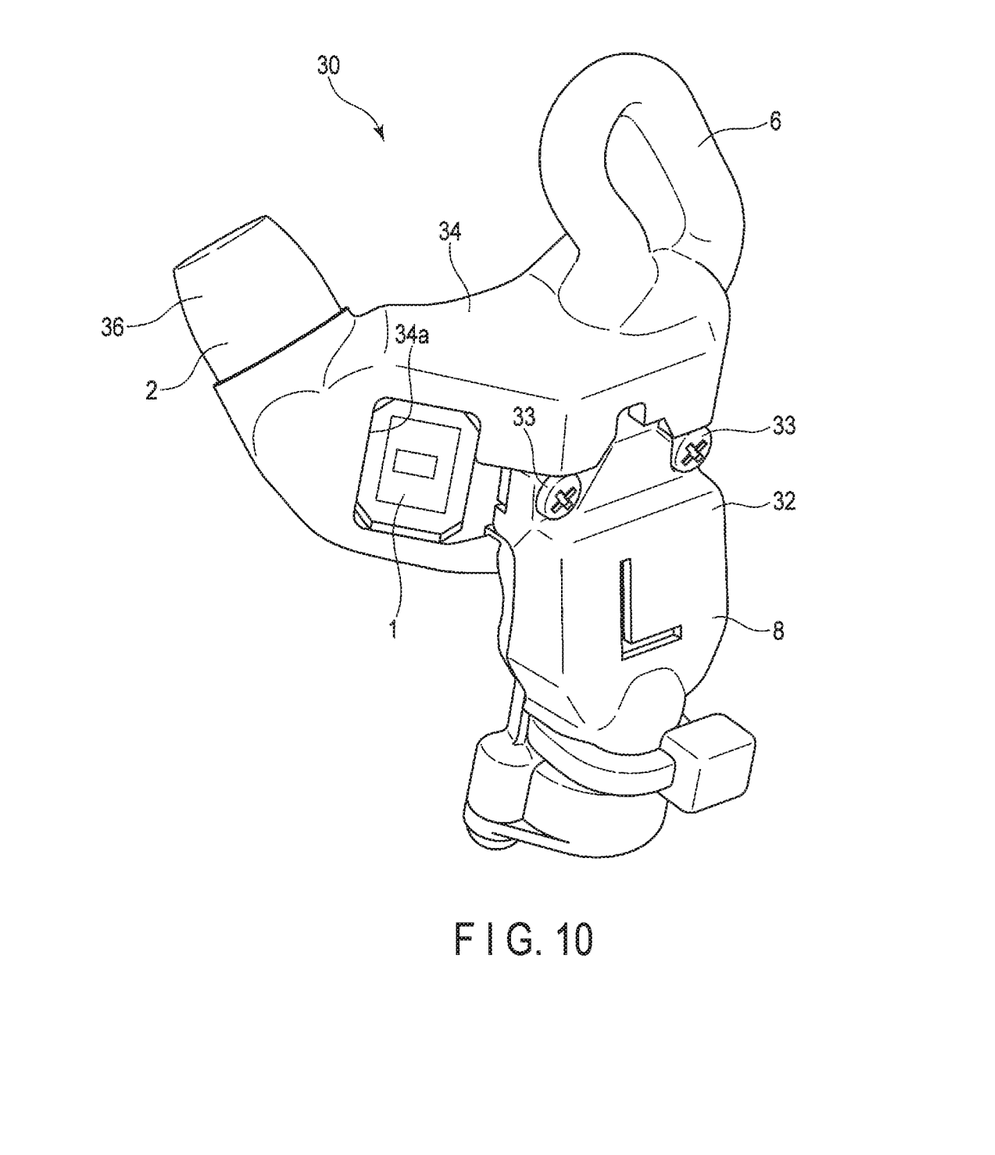
FIG. 10 is a perspective view showing a biological information detection device according to a second embodiment of the present invention.
Figure 11:
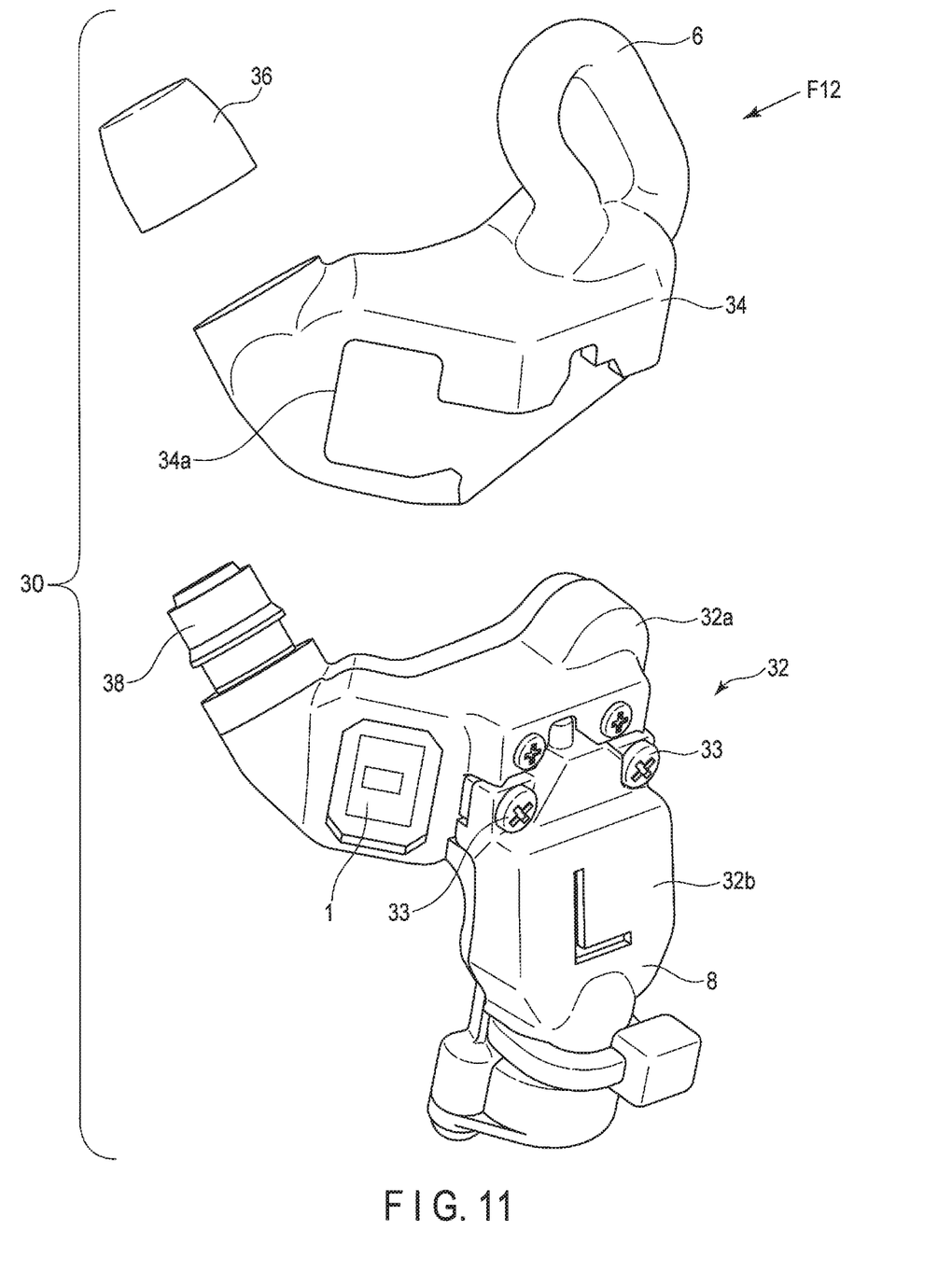
FIG. 11 is an exploded perspective view of the biological information detection device in FIG. 10.
Figure 12:
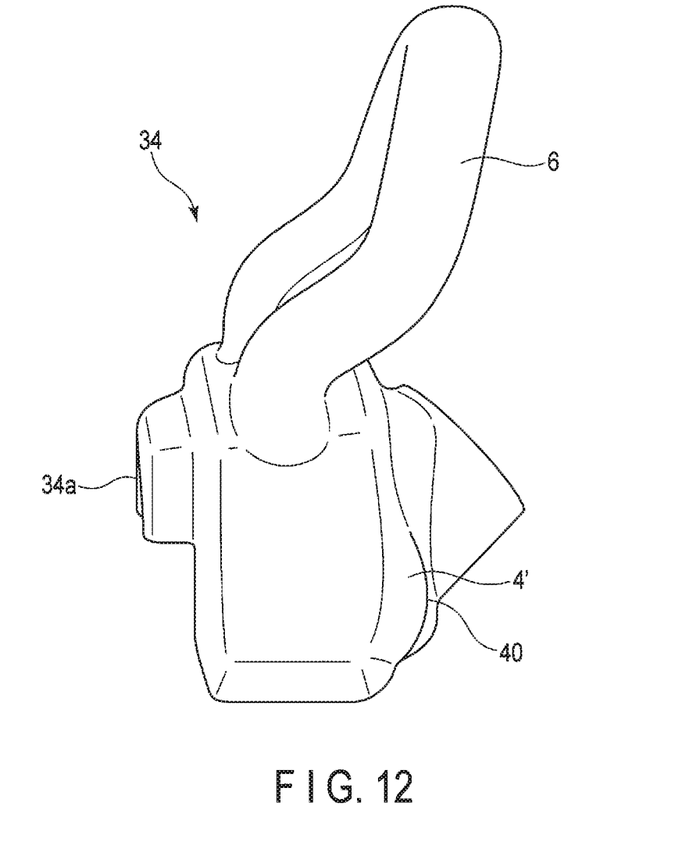
FIG. 12 is a perspective view of a cover in FIG. 11, viewed in the direction indicated by arrow F12.

As shown in FIGS. 10 to 12, the biological information detection device 30 (hereinafter also simply referred to as a "device 30") includes an insertion portion 2, a pressing portion 4' (FIG. 12), an engagement portion 6, a positioning portion 8, and a sensor 1. The positions and angles of the pressing portion 4', engagement portion 6, positioning portion 8, and sensor 1 with respect to the insertion portion 2 are approximately the same as those of the device 10 of the first embodiment.

As shown in FIG. 11, the device 30 includes a main body 32 in which a sensor 1 is fixed, a cover 34, and a cap 36. The main body 32 includes a probe 38. The cover 34 externally covers part of the main body 32, and the cap 36 is attached to the tip of the probe 38 projecting from the cover 34. Namely, the device 30 is assembled by putting the cover 34 on the main body 32 to cover the probe 38, and mounting the cap 36 on the tip of the probe 38 projecting from the cover 34.

The main body 32 includes a first member 32a and a second member 32b. The first member 32a is shaped like a box. On the surface of the first member 32a, on the reverse side of the tragus, the sensor 1 is attached. The first member 32a contains therein a substrate and wiring (both not shown) coupled to the sensor 1. Like the first member 32a, the second member 32b is shaped like a box. The second member 32b contains therein wiring of the sensor 1 extending from the first member 32a to the outside. The first and second members 32a and 32b are formed of, for example a resin or a metal. The main body 32 is assembled by placing the second member 32b on the first member 32a and fixing them to each other by a screw 33.

The cover 34 is detachably attached to the main body 32 to externally cover the first member 32a of the main body 32. The pressing portion 4' and engagement portion 6 are formed integrally with the cover 34. The cover 34 includes a window 34a, to expose the sensor 1. The cover 34 is formed of an elastic member, such as an elastomer.

The cap 36 has a cylinder-like shape, and is fitted and attached to the tip of the probe 38 of the main body 32. The cap 36 is formed of, for example, a urethane-based elastomer, a silicon-based elastomer, or a fluorine-based elastomer. The cap 36 functions as the insertion portion 2 inserted into the ear canal 21 of the ear. The portion of the cover 34 between the cap 36 and the sensor 1 is accommodated in the neighborhood of the entrance of the ear canal 21, and can also be regarded as part of the insertion portion 2. The second member 32b of the main body 32 functions as the positioning portion 8 for fitting in the incisura intertragica 28 of the ear. The positioning portion 8 is part of the main body 32 and does not include the cover 34.

As shown in FIG. 12, the pressing portion 4' has a shape such that part of the cover 34 bulges out like a dome, and has a hollowed-out or solid structure. The structure and function of the pressing portion 4' will be described in detail later. The engagement portion 6 extends to be inclined toward the cymba conchae 26 in the state where the insertion portion 2 is inserted into the ear canal 21.

The device 30 having the above structure is worn on the ear in the same manner as the device 10 of the first embodiment. Namely, the insertion portion 2 is inserted into the ear canal 21, and the engagement portion 6 is inserted between the antihelix 25 and the cymba conchae 26 with the pressing portion 4' pressed against the cavum conchae 24 so that the positioning portion 8 is disposed in the incisura intertragica 28 between the tragus 22 and the antitragus 27.

Like the first embodiment, the present embodiment provides the device 30 with the pressing portion 4', the engagement portion 6, and the positioning portion 8, and thus enables the device 30 to be worn in such a manner as to fit the ear. When the device 30 is worn on the ear, the pressing portion 4' receives a reaction force of the cavum conchae 24, the engagement portion 6 receives reaction forces of the antihelix 25 and the cymba conchae 26, and the positioning portion 8 receives a reaction force of the incisura intertragica 28. These reaction forces rotate the main body 32 about a point around the base of the insertion portion 2 on the main body 32 side to press the sensor 1 against the portion for detection 23 on the back of the tragus 22.

When the device 30 of the present embodiment is used, the same advantages as those of the device 10 of the first embodiment can be produced; namely, the blood flow detection accuracy can be improved, and reliability can be improved. In addition, the device 30 of the present embodiment can tolerate wider variations in ear size than the device 10 of the first embodiment, and thus can fit a wider variety of ears.

Hereinafter, the shape and function of the pressing portion 4' of the biological information detection device 30 according to the second embodiment will be described with reference to FIGS. 12 to 18 in comparison with the device 10 of the first embodiment. In FIGS. 13 to 18, hatching indicating a cross section of the ear is omitted for improved clarity.

First, the shape of the pressing portion 4' will be described.

As shown in FIG. 12, the pressing portion 4' has a shape such that it bulges out like a dome as described above, and has a top 40 at which the pressing portion 4' projects most toward the cavum conchae 24 side. The volume of the pressing portion 4' of the device 30 that bulges toward the cavum conchae 24 is smaller than the volume of the bulged portion of the pressing portion 4 of the device 10, which has the same size as the device 30. The top 40 of the pressing portion 4' is disposed to correspond to a lower part of the main body 32, and is positioned lower than the top of the pressing portion 4 of the device 10 of the first embodiment. Here, "lower" means a direction as viewed from the wearer of the device 30, and is a direction approximately from the engagement portion 6 to the positioning portion 8 in the state where the device 30 is worn on the ear. In other words, the pressing portion 4' of the device 30 has a shape such that the top 40 of the pressing portion 4' is in contact with the cavum conchae 24 at a position lower than an approximate center of the cavum conchae 24 in the state where the insertion portion 2 is inserted into the ear canal 21.

Namely, the top 40 of the pressing portion 4' is at a position farther from the engagement portion 6 than the top of the pressing portion 4 of the device 10 of the first embodiment. In other words, the device 30 of the second embodiment differs from the device 10 of the first embodiment in that, assuming that the top of the pressing portion 4 of the device 10 of the first embodiment is at the vertical center of the main body 12, the top 40 of the pressing portion 4' is at a lower position than the top of the pressing portion 4.

Next, the function of the pressing portion 4' will be described in comparison with the pressing portion 4 of the device 10 of the first embodiment.

Figure 13:
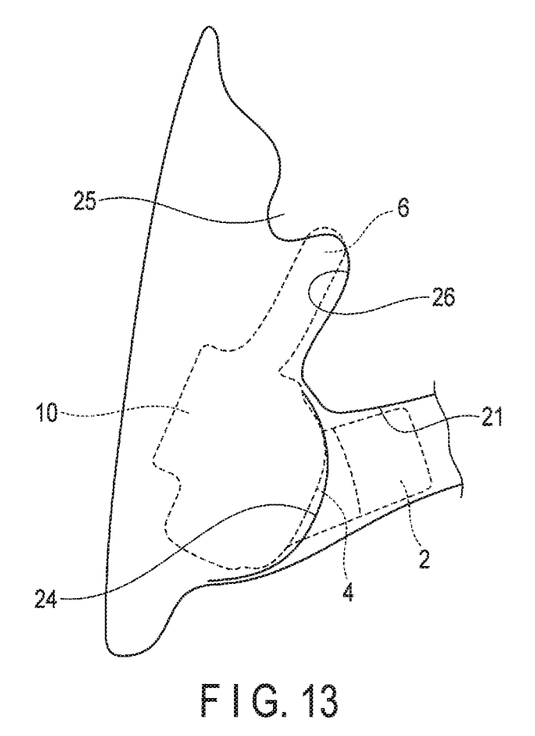
FIG. 13 is a view showing a state where the biological information detection device in FIG. 1 is worn on an average-size left ear.

As shown in FIG. 13, when the device 10 of the first embodiment is worn on an average-size ear, the entire pressing portion 4 easily comes into close contact with the cavum conchae 24 and the engagement portion 6 is also easily inserted between the antihelix 25 and the cymba conchae 26 in the state where the insertion portion 2 is inserted into the ear canal 21 to a predetermined extent. In other words, the device 10 of the first embodiment has a shape that enables close contact of the pressing portion 4 with the cavum conchae 24 with no gap therebetween and enables proper insertion and disposition of the engagement portion 6 between the antihelix 25 and the cymba conchae 26, through insertion of the insertion portion 2 into the ear canal 21 in a proper state.

Figure 14:
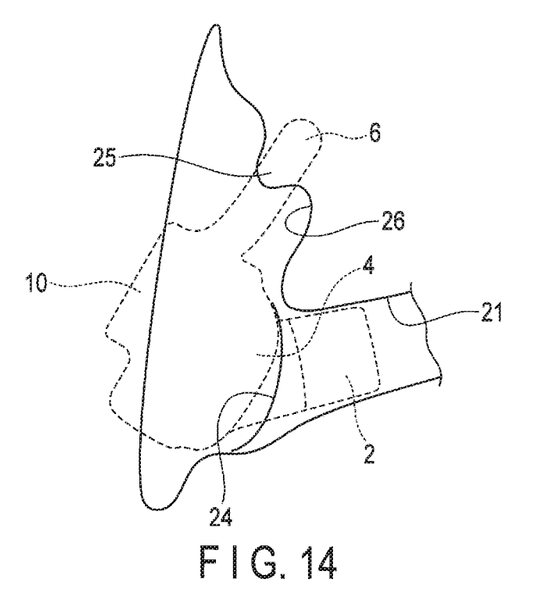
FIG. 14 is a view showing a state where the biological information detection device in FIG. 1 is worn on a relatively small left ear.

However, when the device 10 designed to fit an average-size ear as described above is worn on a relatively small ear as shown in FIG. 14, the device 10 may not easily fit into the ear. In this case, the device 10 can be worn on the ear by deforming the engagement portion 6 by a larger amount so that the engagement portion 6 is pushed in between the antihelix 25 and the cymba conchae 26. In this case, however, the device 10 may easily fall out of the ear during use, and may also cause pain when the device 10 is worn for a long time.

Figure 15:
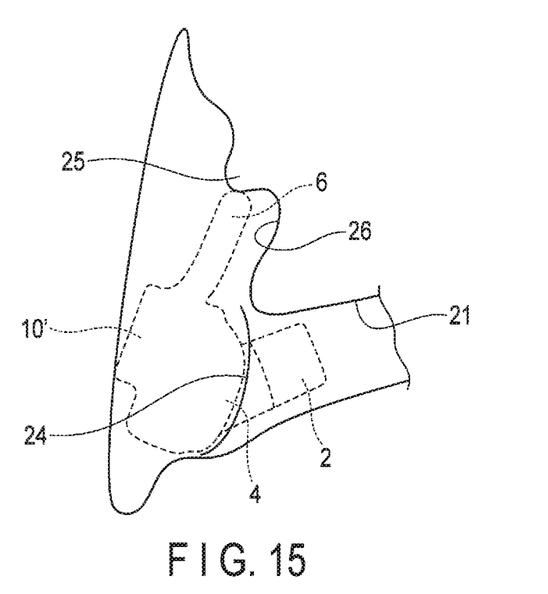
FIG. 15 is a view showing a state where the biological information detection device in FIG. 1 reduced in size is worn on a relatively small left ear.

To eliminate such a problem, it is conceivable to reduce the overall size of the device 10 in accordance with the relatively small ear as shown in FIG. 15. In this case, preparation of multiple types of devices 10 in different sizes for respective sizes of ears suffices. However, in this case, multiple types of devices 10 in different sizes need to be manufactured, which requires different manufacturing lines for the respective sizes and makes management of inventory complicated, and thereby increases the workload and increases the manufacturing costs.

Figure 16:
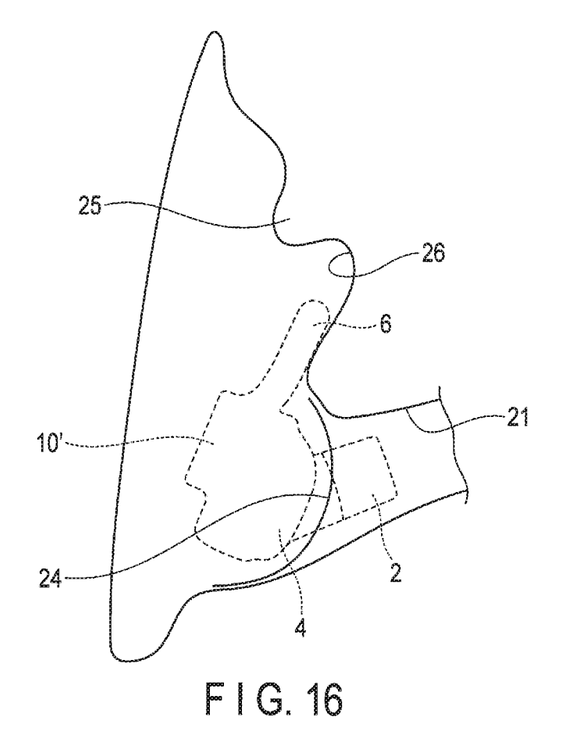
FIG. 16 is a view showing a state where the biological information detection device in FIG. 15 is worn on an average-size left ear.

Therefore, it is conceivable to design the device 10 to have a smaller size than the size for an average-size ear to enable the device 10 to be worn on all ears of different sizes. In this case, however, as shown in FIG. 16, when the device 10' designed to have a smaller size is worn on an average-size ear, the insertion portion 2 cannot be inserted into the ear canal 21 to a predetermined depth, and a gap is formed between the pressing portion 4 and the cavum conchae 24; accordingly, the engagement portion 6 may not reach between the antihelix 25 and the cymba conchae 26.

Therefore, the present embodiment enables the device 30 to be worn on all ears of different sizes by lowering the top 40 of the pressing portion 4' rather than reducing the overall size of the device 30 in comparison to the size of the device 10.

Figure 17:
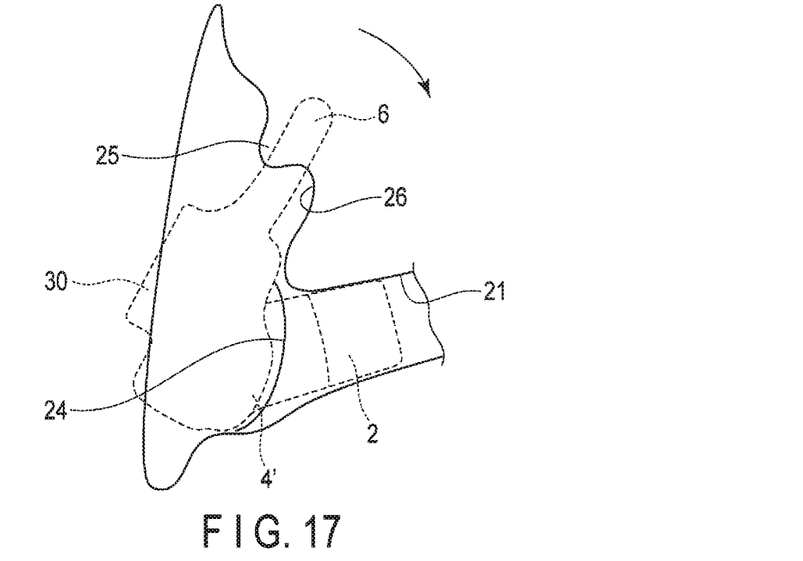
FIG. 17 is a view showing a state where the biological information detection device in FIG. 10 is worn on a relatively small left ear.

For example, as shown in FIG. 17, when the device 30 of the same size as the device 10 is worn on a relatively small ear, the pressing portion 4' easily comes into close contact with the cavum conchae 24 as the volume of the pressing portion 4' bulged out toward the cavum conchae 24 is smaller than that of the device 10, whereby the device 30 fits the ear. In this case, the device 30 slightly rotates clockwise in FIG. 17 about a point around the base of the insertion portion 2 on the main body 32 side, thereby making the gap between the pressing portion 4' and the cavum conchae 24 smaller, and making the pressing portion 4' more easily come into close contact with the cavum conchae 24. The term "clockwise" in FIG. 17 is the direction indicated by the arrow in the figure in which the device 30 rotates in a direction that makes the engagement portion 6 move closer to the head about an imaginary axis extending in the front-back direction as viewed from the wearer of the device 30 and passing through the vicinity of the above-mentioned base.

Figure 18:
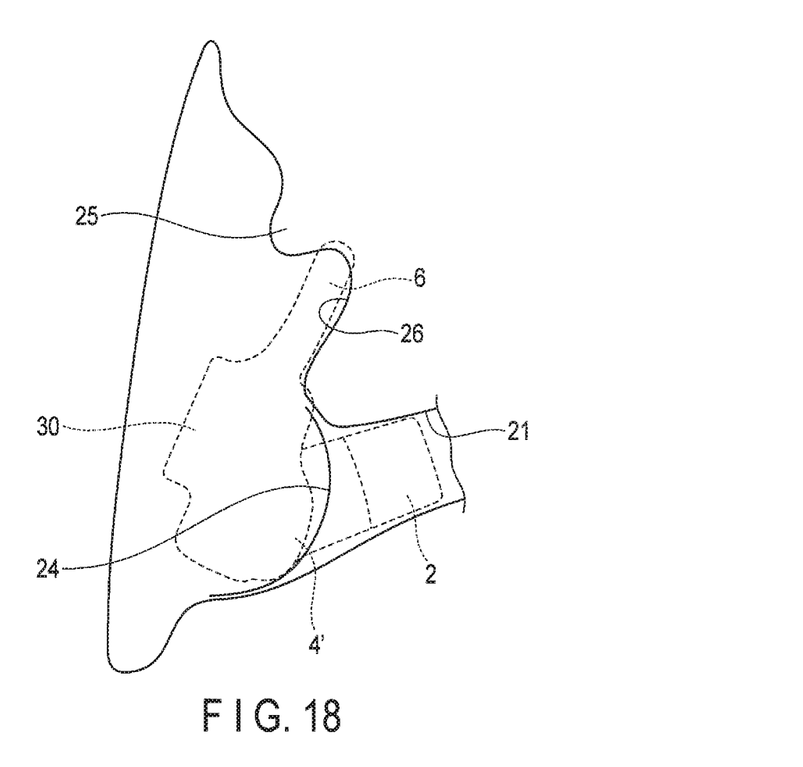
FIG. 18 is a view showing a state where the biological information detection device in FIG. 10 is worn on an average-size left ear.

In contrast, as shown in FIG. 18, when the device 30 of the same size is worn on an average-size ear, a gap is formed between the upper part of the pressing portion 4' and the cavum conchae 24 equal to the amount by which the top 40 is lowered. The gap is assumed to enhance the clockwise rotation of the device 30 in FIG. 18 in comparison with the device 10 of the first embodiment. The term "clockwise" in FIG. 17 is the direction indicated by the arrow in the figure in which the device 30 rotates in a direction that makes the engagement portion 6 move closer to the head about an imaginary axis extending in the front-back direction as viewed from the wearer of the device 30 and passing through the vicinity of the above-mentioned base.

However, the pressing portion 4' with the lowered top 40 fits the lower surface of the cavum conchae 24, the insertion portion 2 is inserted into the ear canal 21 to a predetermined depth, and the engagement portion 6 is pushed in between the antihelix 25 and the cymba conchae 26; therefore, the clockwise rotation is restricted, and the device 30 is firmly worn on the ear. This prevents the device 30 from being unsteady with respect to the ear, enables the sensor 1 to come into close contact with the cavum conchae 24 with no inclination, and can improve detection accuracy of biological information and improve quality. In this case, even if the insertion portion 2 is omitted, the pressing portion 4' fits the lower surface of the cavum conchae 24 and the engagement portion 6 is pushed in between the antihelix 25 and the cymba conchae 26; therefore, the device 30 can be worn in such a manner as to tightly fit the ear.

As described above, the second embodiment can tolerate wider variations in size of ears, enable the device 30 to fit ears with a wider variety of sizes, and eliminate the necessity for manufacturing devices 30 in different sizes for respective ear sizes. Therefore, the device 30 of the second embodiment can reduce the manufacturing costs in comparison with the device 10 of the first embodiment.

The invention of the present application is not limited to the embodiment described above, and can be modified in the implementation stage without departing from the scope of the invention. In addition, the embodiments may be suitably implemented in combination, in which case a combined effect is obtained. Furthermore, inventions in various stages are included in the above-described embodiments, and various inventions can be extracted by a combination selected from a plurality of the disclosed configuration requirements. For example, even if some configuration requirements are removed from all of the configuration requirements shown in the embodiments, if the problem described in the column of the background of the invention can be solved, and an effect is obtained, a configuration from which this configuration requirement is removed can be extracted as an invention.

For example, described in the second embodiment is the device 30 including the insertion portion 2, the pressing portion 4', the engagement portion 6, and the positioning portion 8; however, even when the device 30 does not include the insertion portion 2 or the engagement portion 6, the device 30 can fit average-size ears. In this case, the device can be prevented from being unsteady by bringing the pressing portion 4' into contact with the back of the tragus 22 and lower part of the cavum conchae 24.

In addition, described in the second embodiment is the case where the top 40 of the pressing portion 4' is lowered from the center of the cavum conchae 24; however, the device 30 may better fit an ear when the top 40 is shifted upward, forward, or backward, depending on the shape of the ear. In other words, the top 40 of the pressing portion 4' may be positioned in accordance with the shape of the ear, and the advantages can be produced by bringing the top 40 in contact with a portion other than the center of the cavum conchae 24.

The invention claimed is:

1. A biological information detection device comprising:
   a main body;
   a sensor arranged on a first surface of the main body, the sensor being configured to detect biological information from a portion of a tragus facing an ear canal;
   an insertion portion, wherein a base of the insertion portion is arranged apart from the sensor and extends from a second surface of the main body; and
   a first contact portion and a second contact portion configured to bring the sensor into contact with the portion of the tragus,
   wherein the first contact portion extends from the second surface of the main body and is configured to contact a cavum conchae of the wearer in a state where the insertion portion is inserted into the ear canal to generate a first reaction force on the main body,
   wherein the second contact portion is provided between the first surface and the second surface of the main body and configured to contact an antihelix and/or a cymba conchae of the wearer in the state where the insertion portion is inserted into the ear canal to generate a second reaction force on the main body,
   wherein the second contact portion comprises:
      a first end that extends from the main body;
      a second end that extends from the main body separately from the first end; and
      an antihelix-side contact portion, disposed away from the main body and continuous with the first end and the second end, configured to contact the antihelix and/or the cymba conchae,
   wherein the first end is closer to the insertion portion and the first contact portion that extend from the second surface of the main body than the second end, and wherein, in a state where the insertion portion is inserted into the ear canal, the first reaction force and the second reaction force act to rotate the main body to a side of the tragus about a point around the base of the insertion portion to press the sensor against the portion of the tragus.

2. The biological information detection device according to claim 1, further comprising:
a positioning portion provided in the main body and configured to contact with an incisura intertragica of the ear of the wearer.

3. The biological information detection device according to claim 1, further comprising:
an elastically-deformable cover configured to cover an exterior of the main body,
wherein the elastically-deformable cover is formed integrally with the first contact portion and the second contact portion.

4. The biological information detection device according to claim 2, further comprising:
an elastically-deformable cover configured to cover an exterior of the main body,
wherein the elastically-deformable cover is formed integrally with the first contact portion and the second contact portion.

5. The biological information detection device according to claim 1,
wherein the first contact portion comprises a top configured to be brought into contact with a part other than a center of the cavum conchae.

6. The biological information detection device according to claim 5,
wherein the top of the first contact portion is configured to be brought into contact with a lower part of the cavum conchae.

* * * * *